United States Patent [19]

Minoshima et al.

[11] Patent Number: 4,717,663

[45] Date of Patent: Jan. 5, 1988

[54] METHOD OF PRODUCING XANTHAN GUM

[75] Inventors: Ryouichi Minoshima; Osamu Yamada, both of Yokohama, Japan

[73] Assignee: The Nisshin Oil Mills, Ltd., Tokyo, Japan

[21] Appl. No.: 784,897

[22] Filed: Oct. 7, 1985

[30] Foreign Application Priority Data

Oct. 12, 1984 [JP] Japan ................................. 59-212450
Oct. 12, 1984 [JP] Japan ................................. 59-212451

[51] Int. Cl.$^4$ ..................... C12P 19/06; C12N 1/38; C12R 1/64
[52] U.S. Cl. ................................... 435/104; 435/244; 435/910
[58] Field of Search ............................... 435/104, 244

[56] References Cited

U.S. PATENT DOCUMENTS 4,377,637 3/1983 Weisrock .......................... 435/104
4,444,792 4/1984 Schwartz et al. .............. 435/104 X

*Primary Examiner*—Lionel M. Shapiro
*Attorney, Agent, or Firm*—Bacon & Thomas

[57] ABSTRACT

Xanthan gum can be produced by culturing a Xanthan gum producing microorganism of genus Xanthomonas under aerobic conditions in an aqueous culture medium. The medium contains an assimilable carbon source and at least one additive selected from the group consisting of pantothenic acid, thiamine, and derivatives thereof including salts and esters.

40 Claims, 2 Drawing Figures

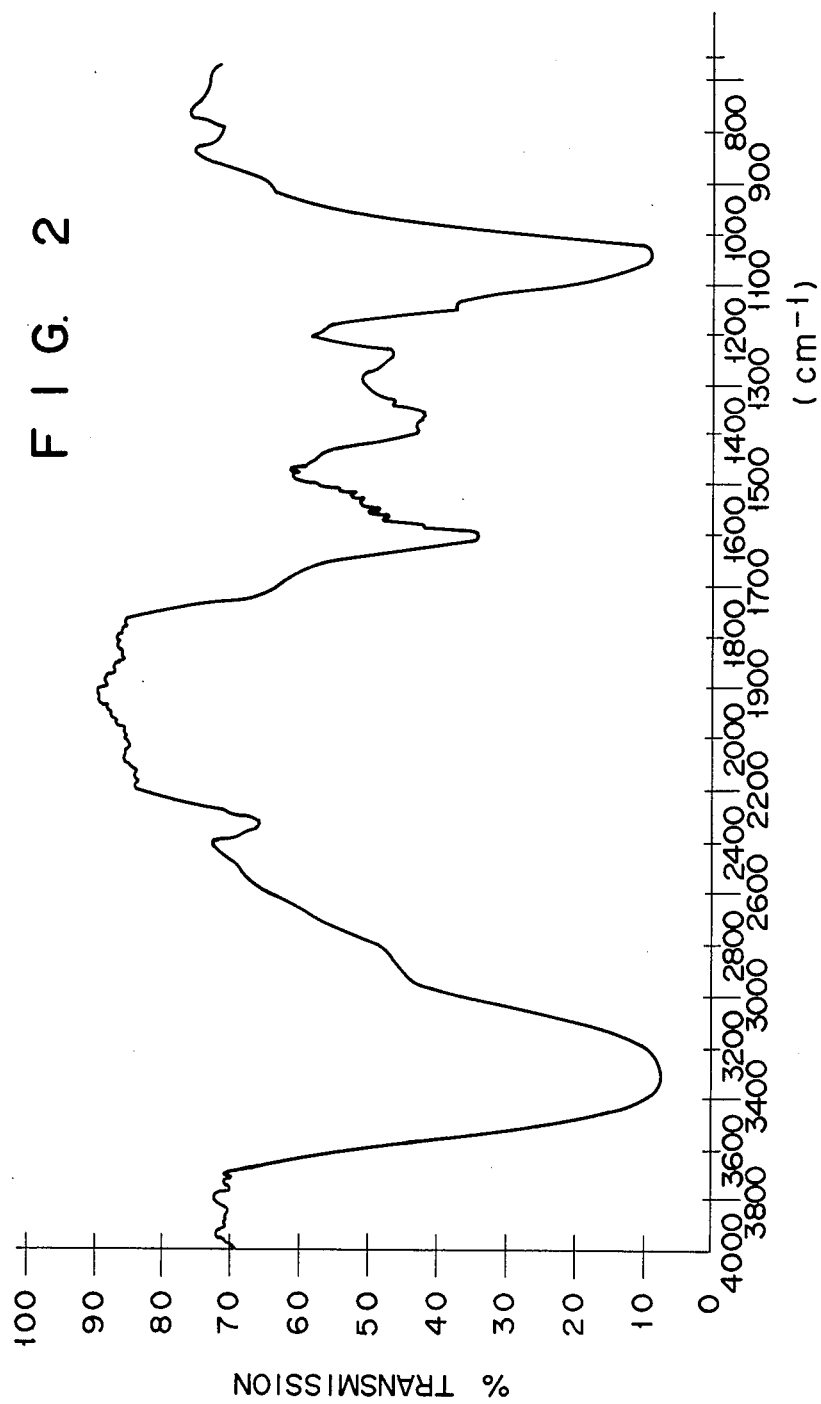

METHOD OF PRODUCING XANTHAN GUM

BACKGROUND OF THE INVENTION

1. Field of the Invention

The present invention relates to a method of producing Xanthan gum and, more particularly, to a method of producing Xanthan gum by culturing microorganisms in a specified culture medium.

2. Description of the Prior Art

Water-soluble viscous polysaccharides or gums include gum arabic, Xanthan gum, guar gum, and tragacanth gum. These gums are widely used in various industries including food, paint, paper making, and petroleum, and demand for such gums is increasing. Among these gums, Xanthan gum obtained by microorganic fermentation has excellent viscosity increasing effect, emulsification/stablization effect, particle/cell dispersion effect, and stabilizing effect against temperature changes, salts and pH. In view of these properties, the industrial application field of Xanthan gum as an effective additive is increasing.

Xanthan gum is conventionally produced by aerobic culture of a microorganism of genus Xanthomonas, e.g., *Xanthomonas campestris, X. carotae* or *X. phaseoli* in a culture medium consisting of a carbon source (e.g., glucose, sucrose, molasses, or starch), peptone, nitrogen, magnesium and trace amounts of other components. After culturing, the culture medium is sterilized, and Xanthan gum is allowed to precipitate by addition of an alcohol (e.g., ethanol or isopropyl alcohol). The precipitate is dried. Specific examples of microorganisms used in the production of Xanthan gum include *X. campestris* "NRRL B-1459" (Japanese Patent Disclosure No. 58-165798) and "ATCC 13951" (Japanese Patent Disclosure No. 58-146290).

However, Xanthan gum obtained by culturing conventional microorganisms of genus Xanthomonas using conventional culture media is significantly colored and must be bleached before industrial application. The bleaching process renders the culture process complex. In addition, this bleaching process must be intensive, thereby further complicating the culture process and increasing its cost.

SUMMARY OF THE INVENTION

It is, therefore, an object of the present invention to provide a method of producing Xanthan gum of low chromaticity using a microorganism of genus Xanthomonas.

According to the present invention, there is provided a method of producing Xanthan gum, comprising:

culturing a Xanthan gum producing microorganism of genus Xanthomonas under aerobic conditions in an aqueous culture medium comprising an assimilable carbon source and at least one additive selected from the group consisting of pantothenic acid, thiamine, and derivatives thereof (including salts and esters), thereby producing Xanthan gum; and recovering the Xanthan gum.

According to the method of the present invention, Xanthan gum of very light color, i.e., low chromaticity can be produced. The bleaching step which is conventionally required can be either omitted or replaced with a light bleaching process, thus providing an advantageous method.

BRIEF DESCRIPTION OF THE DRAWINGS

FIG. 2 is an infrared spectrum of commercially available Xanthan gum.

DESCRIPTION OF THE PREFERRED EMBODIMENTS

Figure 1:
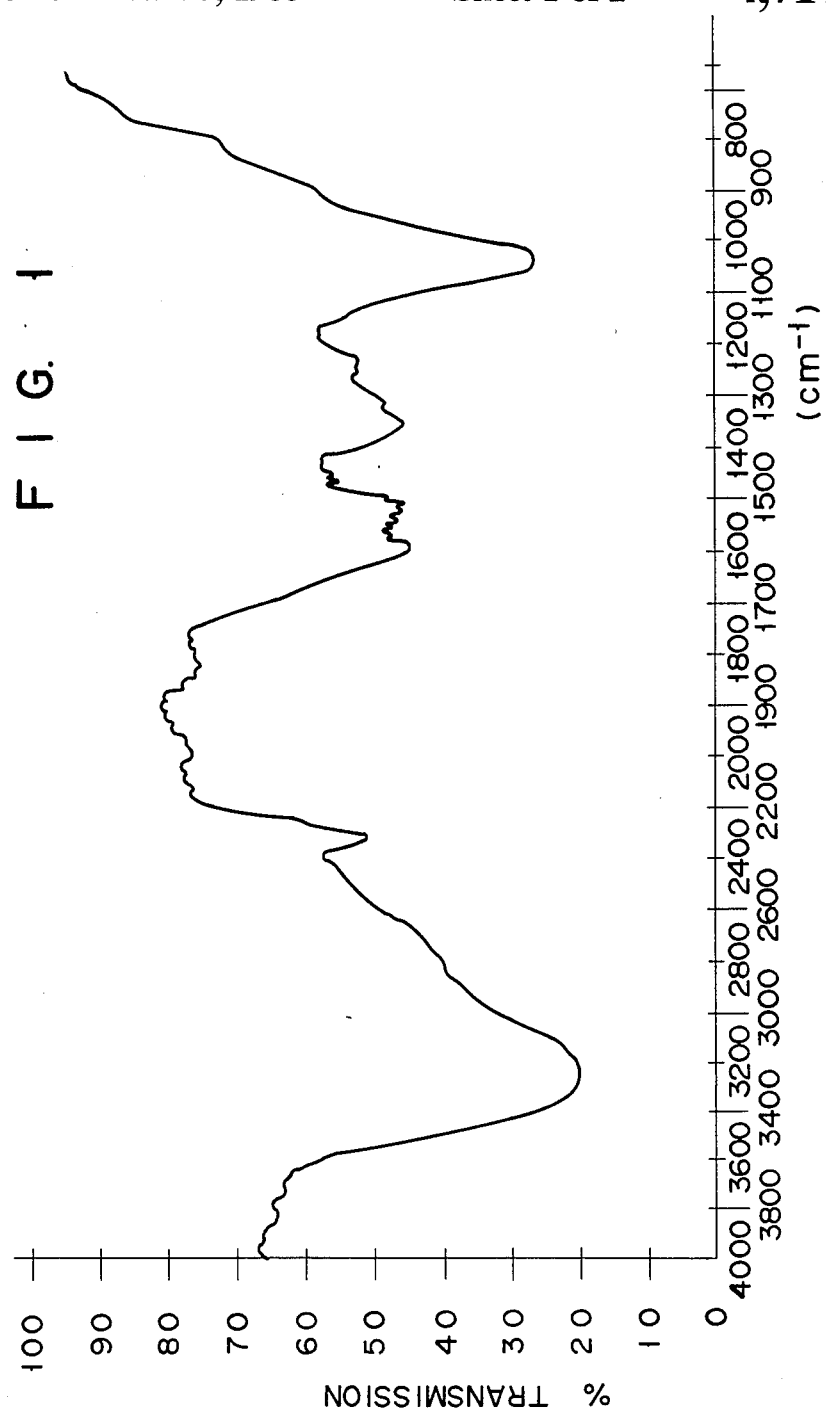
FIG. 1 shows an infrared spectrum of a fermentation product obtained by the method of the present invention.

The present inventors have made extensive studies of the production of Xanthan gum of low chromaticity using a microorganism of genus Xanthomonas. As a result of such studies, the present inventors have found that this object can be accomplished by adding pantothenic acid, thiamine and/or derivatives thereof to a culture medium containing an assimilable carbon source, and culturing the selected microorganism using the culture medium.

Examples of Xanthan gum producing microorganisms of genus Xanthomonas include *X. campestris, X. carotae, X. phaseoli, X. begoniae,* and *X. incanae.* Among these microorganisms, *X. campestris* "NRRL B-1459", "ATCC 13951" and "IFO (Institute for Fermentation, Osaka) 13551" are preferred. It had not been known that *X. campestris* "IFO 13551" produces Xanthan gum, and the phenomenon has now been found out by the present inventors for the first time.

An aqueous culture medium used for fermentation by a microorganism of genus Xanthomonas according to the present invention contains a carbon source and a predetermined additive(s). The culture medium preferably contains a nitrogen source, a phosphate, a magnesium salt, and trace amounts of other components which are conventionally contained.

A conventionally known carbon source can be used. Examples of such a carbon source include sugars (e.g., glucose, sucrose, xylose, molasses, starch, maltose or dextrin), and/or polyhydric alcohols (e.g., glycerin, mannitol or sorbitol). One or more such carbon sources can be used. The carbon source is contained in the culture medium in an amount of 1 to 5% by weight and preferably in an amount of 2 to 4% by weight.

A nitrogen source can be a known nitrogen source and examples of such a nitrogen source may include ammonium nitrate, sodium nitrate, urea, sodium glutamate, alanine, peptone, yeast extract, and malt extract. One or more such nitrogen sources can be used. The nitrogen source is contained in the culture medium in an amount of 0.01 to 5% by weight and preferably in an amount of 0.1 to 1% by weight.

Examples of phosphates may include potassium dihydrogenphosphate, dipotassium hydrogenphosphate, sodium dihydrogenphosphate, and disodium hydrogenphosphate. The phosphate is contained in the culture medium in an amount of 0.01 to 5% by weight and preferably in an amount of 0.1 to 1% by weight.

Examples of magnesium salts may include magnesium phosphate, magnesium nitrate, and magnesium sulfate. The magnesium salt is contained in the culture medium in an amount of 0.01 to 1% by weight and preferably in an amount of 0.01 to 0.5% by weight.

The trace amount components may be one or more of ferrous chloride, ferric chloride, ferrous nitrate, ferric nitrate, ferrous phosphate, ferric phosphate, zinc sulfate, zinc chloride, zinc nitrate, and zinc phosphate. The trace amount component content in the culture medium is, suitably, 0.001 to 0.01% by weight and, preferably, 0.001 to 0.005% by weight.

The characteristic component of the present invention, i.e., pantothenic acid, thiamine, and/or salts, esters or derivatives thereof can be contained in the culture medium in an amount of 0.0001 to 0.1% by weight and preferably in an amount of 0.001 to 0.05%. When the content of this component is less than 0.0001%, an effect of addition cannot be obtained in viscosity, Xanthan gum concentration and chromaticity of the fermented solution (see Table 2 below). When the content of this component exceeds 0.1%, chromaticity of the fermented solution is not much improved and the viscosity is slightly lowered. Examples of pantothenic acid or a derivative thereof may include pantothenic acid, sodium pantothenate, potassium pantothenate, calcium pantothenate, methyl pantothenate, ethyl pantothenate, butyl pantothenate and amide pantothenate. Examples of thiamine or a derivative thereof include thiamine, thiamine hydrochloride, thiamine monophosphate, thiamine diphosphate, and thiamine disulfide.

The remaining component of the aqueous culture medium is water.

After the culture medium having the above composition is adjusted to a pH of 7 to 7.2, a microorganism selected from those enumerated above is inoculated in the culture medium. Culture is performed at 25° to 30° C. under air flow and stirring for 75 to 100 hours. After culturing, sterilization is performed at 121° C. and 1 atm for 10 to 15 minutes. Thereafter, potassium chloride and ethanol or isopropyl alcohol are added to allow Xanthan gum to precipitate. The precipitate is dried and pulverized to obtain a Xanthan gum powder.

The above culture conditions are only one example and the present invention is not limited thereto.

The cultured substance obtained in this manner is identified as Xanthan gum from the following facts: the chemical composition obtained by acid hydrolysis reveals a ratio of glucose:mannose:glucuronic acid of 2:2:1, the infrared spectrum coincides with that of Xanthan gum (FIGS. 1 and 2), and the viscosity (cp at 25° C.) of an aqueous solution of a predetermined concentration behaves similarly to that of a Xanthan gum aqueous solution (Table 1).

TABLE 1

| Concentration (%) | Fermentation Product of Present Invention** | Xanthan gum* |
|---|---|---|
| 0.1 | 82 | 98 |
| 0.5 | 330 | 420 |
| 1.0 | 1100 | 950 |

*Fermentation product obtained in Example 1
**Fermentation product of *Xanthomonas campestris* "NRRL B-1459" under the same conditions When Xanthomonas campestris "IFO 13551" was cultured using the culture medium according to the present invention, the fermented solution obtained after sterilization had a chromaticity as shown in Table 2, i.e., very light color as compared to that obtained by the conventional culture medium.

TABLE 2

| Type of Culture Medium | Type of Micro-organism | Properties of Fermented Solution After Sterilization | | |
|---|---|---|---|---|
| | | Viscosity[1] (cps/25° C.) | Xanthan Gum[2] Concentration (%) | Chromaticity[3] (Gardner) |
| Conventional[4] Culture Medium | IFO 13551 | 9000 | 1.8 | G4 |
| | NRRL B-1459 | 9500 | 1.8 | G4 |
| | ATCC 13951 | 9000 | 1.8 | G4 |
| Culture[5] Medium of Present Invention | IFO 13551 | 9800 | 1.8 | G1 |
| | NRRL B-1459 | 10000 | 1.9 | G2 |
| | ATCC 13951 | 10300 | 1.9 | G2 |
| Conventional Culture Medium[4] + Malic Acid (0.2%) | IFO 13551 | 10000 | 1.9 | G5 |
| | NRRL B-1459 | 10500 | 1.9 | G6 |

Note:
[1]Viscosity: Measurement of 200 ml of the fermented solution was performed using B-type rotation viscometer and a rotor No. 3 at 12 rpm.
[2]Xanthan gum concentration: Ten droplets of a saturated KCl aqueous solution were added to 40 g of the fermented solution, and 80 ml of 95% ethanol were added to cause precipitation. The precipitate was washed with ethanol twice and air-dried to provide Xanthan gum. The Xanthan gum concentration was calculated by:
Xanthan gum concentration = {(Xanthan gum yield (g))/(fermented solution amount (g))} × 100
[3]Chromaticity: Measurement was made with a Gardner chromoscope.
[4]Conventional culture medium composition
Glucose 2.5%
Peptone 0.2%
$K_2HPO_4$ 0.5%
$MgSO_4.7H_2O$ 0.1%
$FeCl_2.7H_2O$ 0.001%
Water Balance TABLE 2-continued

| (5)Culture medium composition of present invention | |
|---|---|
| Glucose | 2.5% |
| Sodium glutamate | 0.2% |
| $K_2HPO_4$ | 0.5% |
| $MgSO_4.7H_2O$ | 0.1% |
| $FeCl_2.7H_2O$ | 0.001% |
| Pantothenic acid | 0.001% |
| Thiamine hydrochloride | 0.001% |
| Water | Balance |

Japanese Patent Disclosure No. 58-165798 discloses addition of fumaric acid or malic acid as a specific component of a fermentation culture medium. However, as can be seen from Table 2, when malic acid (0.2%) is added, chromaticity of the fermented solution is increased significantly. When fumaric acid (0.2%) is added, chromaticity is also significantly increased.

EXAMPLE 1

A culture medium was prepared which consisted of 2.5% of glucose, 0.2% of yeast extract, 0.5% of $K_2HPO_4$, 0.1% of $MgSO_4.7H_2$, 0.001% of $FeCl_2\ 7H_2O$, 0.001% of pantothenic acid and the balance of water. An Erlenmeyer flask with a cotton stop was charged with 50 ml of the culture medium. After adjusting the pH to 7.0, sterilization was performed at 121° C. and 1 atm for 15 minutes and 0.5 ml of a suspension of *Xanthomonas campestris* IFO 13551" (microorganism concentration: $2 \times 10^8$ cells/ml) in another portion of the same culture medium were added. Culture was performed at 28° C. under shaking at 250 rpm for 96 hours. After fermentation, sterilization was performed under the same conditions, and the solution was diluted to 4 times with distilled water. The diluted solution was centrifuged to remove the microorganisms. Fifteen milliliters of a saturated KCl aqueous solution and 350 ml of 95% ethanol were added to the solution to cause precipitation. The precipitate was washed with an equal amount of ethanol twice and then washed with 200 ml of acetone three times, and the crystals were air-dried to provide fibrous white crystals (0.98 g).

The fermented solution had a viscosity of 9,900 cps/25° C., a crystal concentration of 1.8% and a chromaticity (Gardner) of G1. The refined white crystals had a browning temperature of 160° C., a sugar composition (by acid hydrolysis): glucose:mannose:glucuronic acid of 2:2:1, and an infrared absorption spectrum (FIG. 1) coinciding with that (FIG. 2) of Xanthan gum (Keltrol available from Kelco Inc., USA). A 0.5% aqueous solution of the crystals had a viscosity of 380 cps/25° C. and a 1.0% aqueous solution had a viscosity of 980 cps/25° C.

EXAMPLE 2

A culture medium was prepared which consisted of 3.5% of glucose, 0.06% of $NH_4NO_3$, 0.5% of $K_2HPO_4$, 0.1% of $MgSO_4.7H_2O$, 0.001% of $FeCl_2.7H_2O$, 0.001% of $ZnSO_4.7H_2O$, 0.001% of sodium pantothenate, 0.001% of thiamine, and the balance of water. Using 20 ml of this culture medium and 1 l of a suspension of *Xanthomonas campestris* "IFO 13551" in another portion of the same culture medium (microorganism concentration: $5 \times 10^6$ cells/ml), culturing was performed in a jar fermenter having a volume of 50 l at 27° C. under air flow of 0.5 V.Air/V.culture medium/min. and agitation at 500 rpm for 80 hours. The cultured product was treated in the same manner as in Example 1.

After sterilization, the fermented solution had a viscosity of 9,800 cps/25° C., a polysaccharide concentration of 1.8%, and a chromaticity (Gardner) of G1.

The refined crystals had the same properties as those of Example 1.

EXAMPLE 3

A culture medium was prepared which consisted of 2.2% of sucrose, 0.6% of alanine, 0.5% of $Na_2HPO_4$, 0.3% of $MgSO_4.7H_2O$, 0.003% of $Fe(NO_3)_2$, 0.001% of $ZnCl_2$, 0.03% of methyl pantothenate, 0.001% of thiamine hydrochloride, and the balance of water. Fermentation was performed in the same manner as in Example 2 using the thus prepared culture and *Xanthomonas campestris* "NRRL B-1459" to provide white crystals (395 g).

The fermented solution had a viscosity of 10500 cps/25° C., a polysaccharide concentration of 1.9%, and a chormaticity (Gardner) of G2. The refined crystals had the same properties as those in Example 1.

EXAMPLE 4

A culture medium was prepared which consisted of 3.0% of maltose, 0.5% of urea, 0.2% of $K_2HPO_4$, 0.1% of $Mg(NO_3)_2$, 0.003% of $FeCl_2.7H_2O$, 0.005% of pantothenic acid, 0.02% of thiamine monophosphate, and the balance of water. Fermentation was performed in the same manner as in Example 1 using the thus prepared culture medium and *Xanthomonas campestris* "ATCC 13951" to provide white crystals.

The fermented solution had a viscosity of 9,700 cps/25° C., a polysaccharide concentration of 1.8%, and a chromaticity (Gardner) of G1. The refined crystals had the same properties as in Example 1.

As described above, it was not known that *Xanthomonas campestris* "IFO 13551" produces Xanthan gum. However, when *Xanthomonas campestris* "IFO 13551" is cultured in a conventional culture medium, i.e., a culture medium which does not contain pantothenic acid, thiamine or a derivative thereof, although of considerably high chromaticity, Xanthan gum can be produced. An example of culture of *Xanthomonas campestris* "IFO 13551" using a conventional culture medium will be described below.

EXAMPLE 5

A culture medium was prepared which consisted of 2.5% of glucose, 0.2% of peptone, 0.5% of $K_2HPO_4$, 0.1% of $MgSO_4.7H_2O$, 0.001% of $FeCl.7H_2O$, and the balance of water. An Erlenmeyer flask with a cotton stopper was charged with 50 ml of this culture medium. After adjusting the pH of the medium to 7.0, it was sterilized at 121° C. and 1 atm for 15 minutes. 0.5 ml of a suspension of *Xanthomonas campestris* "IFO 13551" in another portion of the same culture medium were added, and culture was performed at 28° C. under shaking at 250 rpm for 96 hours. After fermentation, sterilization was performed under the same conditions, the solution was diluted to 4 times with distilled water and the microorganisms were removed by centrifuging. 15 ml of a saturated KCl aqueous solution and 350 ml of 95% ethanol were added to cause precipitation. The precipitate was washed with an equal amount of ethanol twice and then washed with 200 ml of acetone three times and dried under air flow to provide fibrous yellow crystals (0.97 g).

The fermented solution had a viscosity of 900 cps/25° C., a crystal concentration of 1.8%, and a chromaticity (Gardner) of G4. The refined, fibrous yellow crystals had a browning temperature of 160° C., a sugar composition (acid hydrolysis): glucose:mannose:glucuronic acid of 2:2:1, and an infrared spectrum coinciding with that of Xanthan gum (FIG. 2). A 0.5% aqueous solution of the crystals had a viscosity of 380 cps/25° C. and a 1.0% aqueous solution of the crystals had a viscosity of 980 cps/25° C.

What is claimed is:

1. A method of producing Xanthan gum, comprising:
culturing a Xanthan gum producing microorganism of genus Xanthomonas under aerobic conditions in an aqueous culture medium comprising an assimilable carbon source and a vitamin, thereby producing Xanthan gum, said vitamin consisting of pantothenic acid or a derivative thereof including salts and esters, or consisting of thiamine or a derivative thereof including salts and esters, or consisting of a combination of pantothenic acid or a derivative thereof including salts and esters, and thiamine or a derivative thereof including salts and esters; and
recovering the Xanthan gum.

2. A method according to claim 1, wherein the culture medium contains 1 to 5% by weight of the carbon source.

3. A method according to claim 1, wherein the carbon source is one member selected from the group consisting of glucose, sucrose, xylose, molasses, starch, maltose, dextrin, glycerin, mannitol, sorbitol and mixtures thereof.

4. A method according to claim 1, wherein the culture medium contains 0.0001 to 0.1% by weight of the vitamin additive.

5. A method according to claim 4, wherein the pantothenic acid and derivatives thereof are one member selected from the group consisting of pantothenic acid, sodium pantothenate, potassium pantothenate, calcium pantothenate, methyl pantothenate, ethyl pantothenate, butyl pantothenate, amide pantothenate, and mixtures thereof.

6. A method according to claim 4, wherein the thiamine and derivatives thereof are one member selected from the group consisting of thiamine, thiamine hydrochloride, thiamine monophosphate, thiamine diphosphate, thiamine sulfide and mixtures thereof.

7. A method according to claim 1, wherein the culture medium further contains a nitrogen source.

8. A method according to claim 7, wherein the nitrogen source is contained in an amount of 0.01 to 5% by weight.

9. A method according to claim 7, wherein the nitrogen source is one member selected from the group consisting of ammonium nitrate, sodium nitrate, urea, sodium glutamate, alanine, peptone, yeast extract, malt extract and mixtures thereof.

10. A method according to claim 7, wherein the culture medium further contains a phosphate.

11. A method according to claim 10, wherein the phosphate is contained in an amount of 0.01 to 5% by weight.

12. A method according to claim 11, wherein the phosphate is a member selected from the group consisting of potassium dihydrogenphosphate, dipotassium hydrogenphosphate, sodium dihydrogenphosphate, disodium hydrogenphosphate, and mixtures thereof.

13. A method according to claim 10, wherein the culture medium further contains a magnesium salt.

14. A method according to claim 13, wherein the magnesium salt is contained in an amount of 0.01 to 1% by weight.

15. A method according to claim 14, wherein the magnesium salt is one member selected from the group consisting of magnesium phosphate, magnesium nitrate, magnesium sulfate, and mixtures thereof.

16. A method according to claim 13, wherein the culture medium further contains a trace amount component.

17. A method according to claim 16, wherein the trace amount component is contained in an amount of 0.001 to 0.01% by weight.

18. A method according to claim 17, wherein the trace amount component is one member selected from the group consisting of ferrous chloride, ferric chloride, ferrous nitrate, ferric nitrate, ferrous phosphate, ferric phosphate, zinc sulfate, zinc chloride, zinc nitrate, zinc phosphate and mixtures thereof.

19. A method according to claim 1, wherein the culture is performed at a pH of 7 to 7.2.

20. A method according to claim 19, wherein the culture is performed at a temperature of 25° to 30° C.

21. In a method for producing Xanthan gum by culturing a Xanthan gum-producing microorganism of genus Xanthomonas under aerobic conditions in an aqueous culture medium containing an assimilable carbon source and vitamins, wherein the improvement comprises producing Xanthan gum of reduced chromaticity by utilizing an amount of vitamins in the culture medium which does not increase the chromaticity of the produced gum and which are selected from the group consisting of pantothenic acid, derivatives of pantothenic acid, thiamine, derivatives of thiamine, and mixtures thereof.

22. A method according to claim 21, wherein the culture medium contains 1 to 5% by weight of the carbon source.

23. A method according to claim 21, wherein the carbon source is one member selected from the group consisting of glucose, sucrose, xylose, molasses, starch, maltose, dextrin, glycerin, mannitol, sorbitol and mixtures thereof.

24. A method according to claim 21, wherein the culture medium contains 0.0001 to 0.1% by weight of the vitamin additive.

25. A method according to claim 24, wherein the pantothenic acid and derivatives thereof are one member selected from the group consisting of pantothenic acid, sodium pantothenate, potassium pantothenate, calcium pantothenate, methyl pantothenate, ethyl pantothenate, butyl pantothenate, amide pantothenate, and mixtures thereof.

26. A method according to claim 24, wherein the thiamine and derivatives thereof are one member selected from the group consisting of thiamine, thiamine hydrochloride, thiamine monophosphate, thiamine diphosphate, thiamine sulfide and mixtures thereof.

27. A method according to claim 21, wherein the culture medium further contains a nitrogen source.

28. A method according to claim 27, wherein the nitrogen source is contained in an amount of 0.01 to 5% by weight.

29. A method according to claim 27, wherein the nitrogen source is one member selected from the group consisting of ammonium nitrate, sodium nitrate, urea, sodium glutamate, alanine, peptone, yeast extract, malt extract and mixtures thereof.

30. A method according to claim 27, wherein the culture medium further contains a phosphate.

31. A method according to claim 30, wherein the phosphate is contained in an amount of 0.01 to 5% by weight.

32. A method according to claim 31, wherein the phosphate is a member selected from the group consisting of potassium dihydrogenphosphate, dipotassium hydrogenphosphate, sodium dihydrogenphosphate, disodium hydrogenphosphate, and mixtures thereof.

33. A method according to claim 30, wherein the culture medium further contains a magnesium salt.

34. A method according to claim 33, wherein the magnesium salt is contained in an amount of 0.01 to 1% by weight.

35. A method according to claim 34, wherein the magnesium salt is one member selected from the group consisting of magnesium phosphate, magnesium nitrate, magnesium sulfate, and mixtures thereof.

36. A method according to claim 33, wherein the culture medium further contains a trace amount component.

37. A method according to claim 36, wherein the trace amount component is contained in an amount of 0.001 to 0.01% by weight.

38. A method according to claim 37, wherein the trace amount component is one member selected from the group consisting of ferrous chloride, ferric chloride, ferrous nitrate, ferric nitrate, ferrous phosphate, ferric phosphate, zinc sulfate, zinc chloride, zinc nitrate, zinc phosphate and mixtures thereof.

39. A method according to claim 21, wherein the culture is performed at a pH of 7 to 7.2.

40. A method according to claim 39, wherein the culture is performed at a temperature of 25° to 30° C.

* * * * *